United States Patent [19]
Levy et al.

[11] Patent Number: 5,244,796
[45] Date of Patent: Sep. 14, 1993

[54] **CLONED *LEUCONOSTOC MESENTEROIDES* GLUCOSE-6-PHOSPHATE DEHYDROGENASE GENES AND METHOD OF MAKING GLUCOSE-6-PHOSPHATE DEHYDROGENASE**

[75] Inventors: Hans R. Levy, Dewitt; William T. Lee, Syracuse, both of N.Y.

[73] Assignee: Syracuse University, Syracuse, N.Y.

[21] Appl. No.: 596,867

[22] Filed: Oct. 12, 1990

[51] Int. Cl.$^5$ ............ C12N 9/04; C12N 15/11; C12N 15/53
[52] U.S. Cl. ............ 435/190; 435/69.1; 435/172.3; 435/252.33; 435/320.1; 536/23.2; 536/24.3; 935/14; 935/8
[58] Field of Search ............ 435/189, 190, 69.1, 435/252.33, 320.1; 536/27, 23.2, 24.3

[56] References Cited

U.S. PATENT DOCUMENTS

| | | | |
|---|---|---|---|
| 4,652,639 | 3/1987 | Stubinsky | 536/27 |
| 4,686,181 | 8/1987 | Doná | 435/7 |
| 5,137,821 | 8/1992 | Sagai et al. | 435/190 |

OTHER PUBLICATIONS

Levy, H. R., 1988, *Biochemical Society Transactions*, 17: 313-315.
Jaye, M., et al., 1983, *Nucleic Acids Research*, 11(8): 2325-2335.
Bhadbhade, M. M., et al., 1987, *FEBS Letters*, 211(2): 243-246.
Lathe, R., 1985, *Journal of Molecular Biology* 183: 1-12.
Product Description from Boehringer Mannheim Corp. Printed Nov. 1990–Glucose-6-Phosphate Dehydrogenase.
Murphy, Noel B. et al., "Expression of other Gene for NAD-Dependent Glucose-6-Phosphate Dehydrogenase from Leuconostoc Mesenteroides Cloned in *Escherichia coli* K-12". Journal of Bacteriology, vol. 169 No. 1, pp. 334-339, Jan. 1987.

Primary Examiner—Robert A. Wax
Assistant Examiner—William W. Moore
Attorney, Agent, or Firm—Wall and Roehrig

[57] ABSTRACT

The Glc6PD genome of *Leuconostoc mesenteroides* is isolated. Oligonucleotides complementary to sequences upstream and downstream to the Glc6PD genome are prepared and used to amplify the genome by the polymerase chain reaction. The amplified gene is isolated and cloned into pUC19. The recombinant plasmid expresses the gene in *E. coli*.

9 Claims, 6 Drawing Sheets

```
GGATCCTATCTAAAAGCCTACTTCATTTGTTGTACTCCTCATTTGCTTTT     (50)
TTATTATTGTGTAACGAACAGGTGATAAGGTCAAGTGCAAAATTTCACGA     (100)
CAGATATCCAATTTTAGATGATAAACGTTTAAAAAACGCTGAAAACGGTT     (150)
ACTTTTTCCGCTATTTTGCGCTATAATGAAAGTGAATTTAACTAAAAAT     (200)
AAGGGGTACATCATGGTTTCAGAAATCAAGACGTTAGTAACTTTCTTTGG    (250)
              V  S  E  I  K  T  L  V  T  F  F  G      (12)

TGGCACTGGTGACTTGGCCAAGCGTAAGCTTTACCCATCAGTTTTCAATC    (300)
 G  T  G  D  L  A  K  R  K  L  Y  P  S  V  F  N  L    (29)

TTTATAAAAAAGGCTACTTGCAAAAGCATTTTGCCATTGTTGGAACGGCC    (350)
  Y  K  K  G  Y  L  Q  K  H  F  A  I  V  G  T  A      (45)

CGTCAAGCCCTCAATGATGACGAATTCAAACAATTGGTTCGTGATTCAAT    (400)
 R  Q  A  L  N  D  D  E  F  K  Q  L  V  R  D  S  I    (62)

TAAAGATTTCACTGACGATCAAGCACAAGCTGAGGCGTTCATCGAACATT    (450)
  K  D  F  T  D  D  Q  A  Q  A  E  A  F  I  E  H  F   (79)

TCTCATACCGTGCACACGACGTAACAGATGCTGCTTCATACGCTGTTTTA    (500)
  S  Y  R  A  H  D  V  T  D  A  A  S  Y  A  V  L     (95)

AAAGAGGCGATTGAAGAAGCTGCCGACAAATTTGATATCGATGGCAACCG    (550)
 K  E  A  I  E  E  A  A  D  K  F  D  I  D  G  N  R    (112)

CATTTTCTATATGTCAGTTGCGCCACGTTTCTTTGGTACAATTGCCAAAT    (600)
  I  F  Y  M  S  V  A  P  R  F  F  G  T  I  A  K  Y   (129)

ATCTTAAGTCAGAAGGCCTACTAGCTGACACTGGTTACAACCGTTTGATG    (650)
   L  K  S  E  G  L  L  A  D  T  G  Y  N  R  L  M     (145)
```

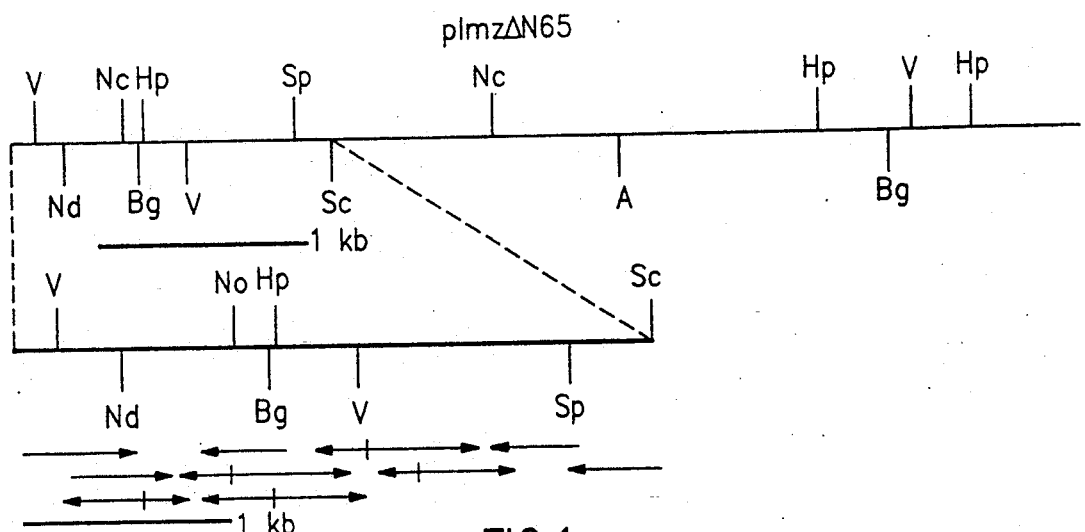
FIG.1
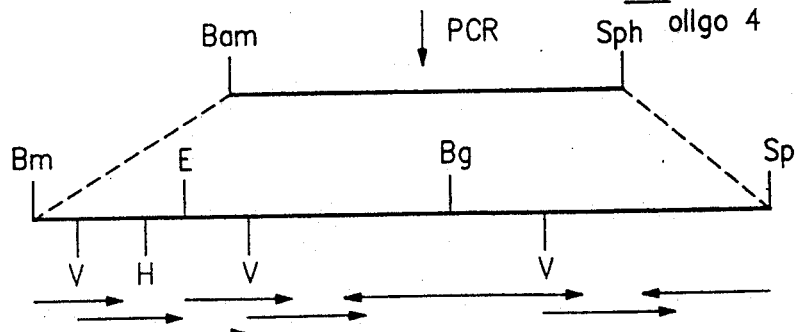
FIG.2A
FIG.2B

```
GGATCCTATCTAAAAGCCTACTTCATTTGTTGTACTCCTCATTTGCTTTT    (50)
TTATTATTGTGTAACAGGTGATAAGGTCAAGTGCAAAATTTCACGA        (100)
CAGATATCCAATTTAGATGATAAACGTTAAAAACGCTGAAAACGGTT       (150)
ACTTTTCCGCTATTTGCGCTATAATGAAAAGTGAATTAACTAAAAAT       (200)
AAGGGGTACATCATGGTTTCAGAAATCAAGACGTTAGTAACTTTCTTTGG    (250)
                     V  S  E  I  K  T  L  V  T  F  F  G  (12)

TGGCACTGGTGACTTGGCCAAGCGTAAGCTTTACCCATCAGTTTTCAATC    (300)
 G  T  G  D  L  A  K  R  K  L  Y  P  S  V  F  N  L      (29)

TTTATAAAAAGGCTACTTGCAAAAGCATTTTGCCAATTGTTGGAACGGCC    (350)
 Y  K  K  G  Y  L  Q  K  H  F  A  I  V  G  T  A         (45)

CGTCAAGCCCTCAATGATGACGATGAATTCAAACAAGCACAAGCTGAGGGCGTTCGTGATTCAAT  (400)
 R  Q  A  L  N  D  D  E  F  K  Q  A  Q  A  E  A  F      (62)

TAAAGATTTCACTGACGATCAAGACCGTAACAGATGCTGCTTCATCGAACATT (450)
 K  D  F  T  D  D  Q  A  Q  L  V  R  D  S  I            (79)

TCTCATACCGTGCACACGATGCTGCTTCATACGCCTGTTTA             (500)
 S  Y  R  A  H  D  V  T  D  A  A  S  Y  A  V  L         (95)

AAAGAGGCGATTGAAGAAGCTGCCGACAAATTTGATATCGATGGCAACCG    (550)
 K  E  A  I  E  E  A  A  D  K  F  D  I  D  G  N  R      (112)

CATTTTCTATATGTCAGTTGCGCCACGTTTCTTTGGTACAATTGCCAAAT    (600)
 I  F  Y  M  S  V  A  P  R  F  F  G  T  I  A  K  Y      (129)

ATCTTAAGTCAGAGAAGGCCCTACTAGCTGACACTGGTTACAACCGTTTGATG (650)
 L  K  S  E  G  L  L  A  D  T  G  Y  N  R  L  M         (145)
```

FIG.3A

```
ATTGAAAAGCCCTTTCGGTACATCATATGACACAGCTGCCGAACTCCAAAA  (700)
 I  E  K  P  F  G  T  S  Y  D  T  A  E  L  Q  N      {162}

TGACTTGGAAAACGGCATTTGATGATAACCAACTATTCCGTATTGACCACT  (750)
 D  L  E  N  A  F  D  D  N  Q  L  F  R  I  D  H  Y   {179}

ACCTTGGTAAGGAAATGGTTCAAAACATTGCTGCCCTTCGCTTTGGTAAC   (800)
 L  G  K  E  M  V  Q  N  I  A  A  L  R  F  G  N      {195}

CCAATTTTCGATGCTGCTTGGAACAAGGATTACATCAAGAACGTTCAAGT   (850)
 P  I  F  D  A  A  W  N  K  D  Y  I  K  N  V  Q  V   {212}

AACATTGTCAGAAGTCTTGGGTGTCGAAGAACGTGCCGGCTACTATGACA   (900)
 T  L  S  E  V  L  G  V  E  E  R  A  G  Y  Y  D  T   {229}

CAGCCGGGTGCATTGCTTGACATGATTCAAAACCACCATGCAAATTGTT    (950)
 A  G  A  L  L  D  M  I  Q  N  H  T  M  Q  I  V      {245}

GGTTGGTTAGCCATGGAAAAACCAGAATCATTCACTGACAAAGACATTCG  (1000)
 G  W  L  A  M  E  K  P  E  S  F  T  D  K  D  I  R   {262}
```

FIG.3B

TGCCGCTAAAAACGCAGCCTTTAATGCTTTGAAGATCTATGATGAAGCAG (1050)
 A  A  K  N  A  A  F  N  A  L  K  I  Y  D  E  A  E   (279)

AAGTTAACAAATACTTTGTTCGTGCACAATATGGCTGCCGGTGATTCAGCT (1100)
 V  N  K  Y  F  V  R  A  Q  Y  G  A  G  D  S  A      (295)

GACTTCAAGCCATACCTTGAAGAATTAGACGTACCTGCTGATTCTAAAAA  (1150)
 D  F  K  P  Y  L  E  E  L  D  V  P  A  D  S  K  N   (312)

CAATACCTTCATCGCCGGCGAATTGCAATTTGATTTGCCACGTTGGGAGG  (1200)
 N  T  F  I  A  G  E  L  Q  F  D  L  P  R  W  E  G   (329)

GTGTCCCATTCTATGTCCGTTCAGGTAAGCGCCTAGCTGCTAAACAGACA  (1250)
 V  P  F  Y  V  R  S  G  K  R  L  A  A  K  Q  T      (345)

CGGGTTGATATCGTCTTTAAGGCTGGCACGTTTAACTTTGGTTCAGAACA  (1300)
 R  V  D  I  V  F  K  A  G  T  F  N  F  G  S  E  Q   (362)

AGAAGCACAAGAAGCTGTCTTGTCAATTATCATTGATCCAAAGGGTGCTA  (1350)
 E  A  Q  E  A  V  L  S  I  I  D  P  K  G  A  I      (379)

TCGAATTGACTTAGGTTGGACTGTATCTGACGCCCAAGTCAGTTGAAGATGCTTTCAACACGT (1400)
 E  L  D  L  G  W  T  V  S  D  A  F  N  T  R        (395)

ACAATTGACTTAGGTTGGACTGTATCTGACGAAGATAAGAAGAACACGCC  (1450)
 T  I  D  L  G  W  T  V  S  D  A  K  K  N  T  P      (412)

AGAACCATACGAACGTATGATTCACGACACTATGAATGGTGATGGCTCTA  (1500)
 E  P  Y  E  R  M  I  H  D  T  M  N  G  D  G  S  N   (429)

FIG. 3C

```
ACTTCGCTGACTGGAATGGGCCGTTTCAATCGCCGTTTGGAAGTTCGTTGATGCT    (1550)
  F  A  D  W  N  G  V  S  I  A  W  K  F  V  D  A           (445)

ATTTCAGCCCGTTTATACCCGCAGATAAAGCACCACTTGAAACTTACAAGTC       (1600)
  I  S  A  V  Y  T  A  D  K  A  P  L  E  T  Y  K  S        (462)

GGGCTCAATGGGTCCTGAAGCATCCGATAAATTATTGGCTGCCAATGGTG         (1650)
  G  S  M  G  P  E  A  S  D  K  L  L  A  A  N  G  D        (479)

ATGCTTGGGTGTTTAAAGGTTAATTAAAGCCCCAAAAAAACGATCCGATTG        (1700)
  A  W  V  F  K  G                                         (485)

TGATCGTTTTTTATTGCCCAATTTACACAGTTTCATCAAGAATCCGTTT          (1750)
TGTTTCACGAAAAAACAGCCGCTAAGTTTTGTACGTAAAGAACCATGCCAGCA      (1800)
CAACAGTAACAAAGTGATGCTTTTGTACGTAAAGAACCCAACAAATGAC          (1850)
ACACCAGATTAACAGAAACACCTAATTTACCACCCCGTGACCCTGATATTT        (1900)
TGTCTGACTAAAAATAGTTTATTCATTAGTGAAAAATTTGACGCTTGAGT         (1950)
TGTGCCATTGAAAGTGGGGATC                                     (1970)
```

FIG.3D

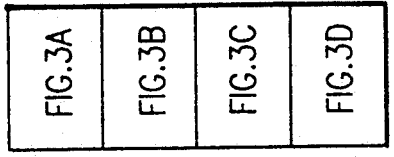

FIG.3

```
AEQVALSRTQVCGILREELFQGDAFHQSDTHIFIIMGASGDLAKKKIYPTIWLFRDGLL   (60)
  ***  ***     **  ****   * ** *****    *
        VSEIKTLVTFFGGTGDLAKRKLYPSVFNLYKKGYL

PENTFIVGYARSRLTVADIRKQSEPFFKATPEEKLKLEDFFARNSYVAGQYDDAASYQRL  (120)
   ***** *    *        ****     ****      *** *  *****
QKHFAIVGTARQALNDDEFKQLVRDSIKDFTDDQAQAEAFIEHFSYRAHDVTDAASYAVL

NSHMNALHLGSQA    NRLFYLALPPTVYEAVTKNIHESC MSQIGWNRIIVEKPFGRDLQSSD  (180)
                 ***** ***              *  *****  ****
KEAIEEAADKFDIDGNRIFYMSVAPRFFGTIAKYLKSEGLLADTGYNRLMIEKPFGTSYDTAA

RLSNHISSLFREDQIYRIDHYLGKEMVQNLMVLRFANRIFGPIWNRDNIACVILTFKEPF   (240)
       *      ***********     *    **  *
ELQNDLENAFDDNQLFRIDHYLGKEMVQNIAALRFGNPIFDAAWNKDYIKNVQVTLSEVL

GTEGRGGYFDEFGIIRDVMQNHLLQMLCLVAMEKPASTNSDDVRDEKVKVLKCISEVQAN   (300)
   *     ***     **         *****           *
GVEERAGYYDTAGALLDMIQNHTMQIVGWLAMEKPESFTDKDIRAAKNAAFNALKIYDEA

NVVLGQYVGNP DGEGEATKGYLDDPTVPRGSTTATFAAVVLYVENER WDGVPFILRCGKA   (360)
      *  *                    *  ***  **  *
EVNKYFVRAQYGAGDSADFKPYLEELDVPADSKNNTFIAGELQFDLPRWEGVPFYVRSGKR

LNERKAEVRLQFHDVAGDIFHQQCKRNELVIRVQPNEAVYTKMMTKKPGMFFNPEESELD   (420)
                  *  *
LAAKQTRVDIVFKAGTFNFGSEQEAVLSIIIDPKGAIELKLNAKSVEDAFNTRTIDLG

LTYGNRYKNVKLPDAYERLILDVFCGSQMHFVRSDELREAWRIFTPLLHQIELEKPKPIP   (480)
                                                  *
WTVSDEDKKNTPEPYERMIHDTMNGDGSNFADWNGVSIAWKFVDAISAVYTADKAPLET

YIYGSRGPTEADELMKRVGFQYEGTYKWVNPHKL                           (514)
  ***  *  *
YKSGSMGPEASDKLLAANGDAWVFKG
```

FIG.4

CLONED *LEUCONOSTOC MESENTEROIDES* GLUCOSE-6-PHOSPHATE DEHYDROGENASE GENES AND METHOD OF MAKING GLUCOSE-6-PHOSPHATE DEHYDROGENASE

This invention was made with government support under Grant No. GM 41085 from the United States Public Health Service, and Grant No. PCM 8309379 from the National Science Foundation. The government has certain rights in the invention.

BACKGROUND OF THE INVENTION

Glucose-6-phosphate dehydrogenase (Glc6PD) from the bacterium *Leuconostoc mesenteroides* has commercial utility in the enzymatic oxidation of glucose 6 phosphate. This enzyme is capable of utilizing either $NAD^+$ or $NADP^+$ as a coenzyme, whereas Glc6PD from other conventional sources such as human erythrocytes or rat liver can utilize $NADP^+$ but show little if any activity with $NAD^+$. *L. mesenteroides* is employed in commercial enzyme immunoassay systems, clinical laboratory determinations such as glucose analysis, and other useful chemical reactions requiring the oxidation of glucose-6-phosphate.

Obtaining Glc6PD by standard enzyme purification methods in commercially practicable amounts has been expensive and difficult. Using recombinant DNA technology, it is possible to produce enzymes such as Glc6PD economically and in large amounts with bacteria such as *E. coli*. Various techniques of gene cloning are known to the art, and others have succeeded in cloning genes for Glc6PD from sources such as *Drosophila melanogaster*, rat liver, and human erythrocytes, the Glc6PD resulting from such genes lacks the desirable properties of that from *Leuconostoc mesenteroides*. Until applicant's invention, it is believed, that no one has successfully cloned the Glc6PD gene from *Leuconostoc mesenteroides*. A purported cloning of the *L. mesenteroides* gene was published by Murphy et al. (*J. Bacteriology*, Vol. 169, pp 334-339, June 1987).

OBJECTS AND SUMMARY OF THE INVENTION

It is therefore an object of the present invention to provide a DNA clone of the *L. mesenteroides* Glc6PD gene, which can be used to economically produce large amounts of Glc6PD.

It is a further object of the invention to provide a plasmid containing the *L. mesenteroides* Glc6PD gene.

It is yet another object of the present invention to provide a method for cloning the gene of L. mesenteroides.

It is still another object of the present invention to provide a method for the production of a plasmid containing the *L. mesenteroides* Glc6PD gene.

It is a further object of the present invention to provide a method for the economical production of Glucose-6-phosphate dehydrogenase derived from a clone of the *L. mesenteroides* Glc6PD gene.

These and other and further objects of the present invention, together with additional features and advantages accruing therefrom will be apparent from the following description of a preferred embodiment of the invention as shown in the accompanying drawings, wherein:

BRIEF DESCRIPTION OF THE DRAWINGS

FIG. 1 is a restriction map of a DNA clone of *L. mesenteroides* Glc6PD gene;

FIG. 2A is a block diagram showing the isolation and amplification of an upstream fragment of the *L. mesenteroides* Glc6PD gene from a plasmid;

FIG. 2B is a diagram of a PCR amplified *L. mesenteroides* Glc6PD gene;

FIG. 3 is a diagram indicating the relationships of FIGS. 3A-3D;

FIGS. 3A-3D are an amino acid sequence map of Glc6PD derived from *L. mesenteroides* gene from a plasmid; and FIG. 4 is an amino acid sequence map comparing the composition of *L. mesenteroides* Glc6PD and human erythrocyte Glc6PD.

DETAILED DESCRIPTION OF A PREFERRED EMBODIMENT

Glucose-6-phosphate dehydrogenase (Glc6PD) from *Leuconostoc mesenteroides* can utilize either $NAD^+$ or $NADP^+$ as coenzyme in the oxidation of glucose-6-phosphate. The enzyme is a dimer with identical subunits, of M.W. 54,800. The kinetic mechanism differs depending on whether $NAD^+$ or $NADP^+$ is used in the reaction. Binding of $NAD^+$ produces a large conformational change in the enzyme.

The genes for Glc6PDs from *Drosophlia melanogaster*, rat liver, and human erythrocyte have been cloned. The cloning of the *L. mesenteroides* Glc6PD gene will allow for the comparison to other Glc6PD sequences and for the design of site directed mutagenesis studies to help determine the enzyme mechanism. This information will be augmented by the 3-dimensional structure of the enzyme which is presently under study.

The cloning of the *L. mesenteroides* Glc6PD gene was described previously. No sequence information was presented in that paper and the results of the cloning of the gene presented here differ from those in that paper.

MATERIALS AND METHODS

Materials. Restriction enzymes, DNA modifying enzymes, pUC19, M13mp18, and M13mp19 were from BRL. Taq polymerase was from Perkin-Elmer Cetus, modified $T_4$ DNA polymerase (Sequenase) from U.S. Biochemical, radionucleotides from New England Nuclear, Geneclean from BIO 101, λGEM11 from Promega, and the ECL gene detection system was from Amersham. All other reagents were analytical grade.

Bacterial strains. *L. mesenteroides* was from the American Type Culture Collection (ATCC 12291). *E. coli* strains DH5α and DH5αF' were provided by Dr. David T. Sullivan (Syracuse University), DH5αMCR was from BRL and MB406 and LE392 were from Promega. Amino acid sequencing.

CNBR Cleavage. The protein was subjected to a 24 hour CNBr cleavage (CNBr 1 mg/ml in 70% formic acid) and then lyophilized three times. The resulting fragments were separated by gel filtration, on 30 cm Biosil TSK 250-TSK 125 columns, in tandem, using 3M guanidine HCl, 50 mM sodium phosphate, 10 mM 2-mercaptoethanol pH 7.0 at 1.0 ml/min isocratic. Five major peaks were collected, dialysed against double distilled $H_2O$ twice in 1000 molecular weight cut-off tubing and lyophilized. Portions of these fractions were re-run on a Waters μBondapak C18 column using various gradients, mostly 25% -65% or, occasionally to 75% B over 80–100 min, where A was 0.1% TFA and B was 0.1% TFA in 80% acetonitrile.

Maleylated Peptides. The protein was dissolved in 2.0 ml of 0.1 M-sodium pyrophosphate buffer at pH 9.0. It was then treated with 1.0 M-maleic anhydride in redistilled dioxane added in 6 portions of 50 μl. During the reaction the pH was maintained at 9.0 with 0.1M NaOH. Tryptic digest of the enzyme occurred in 0.1M ammonium bicarbonate at 37° C. for 4 hrs. The product was lyophilized and run on a Waters μBondapak column under the same conditions as described above.

Thermolysin. Glc6PD was dissolved in 100-mM-NH$_4$HCO$_3$ and 5 mM CaCl$_2$ in the presence of thermolysin at a concentration of 2% enzyme/substrate (w/w). Incubation proceeded at 37° C. for at least 4 hours. The digest was run on a Waters μBondapak reverse phase C18 column, at a flow rate of 1.5 ml/min, with 0–75% B over 150 min where buffer A was 0.1% TFA and buffer B was 0.1% TFA in acetonitrile. Some peptides were further purified using a Beckman Ultrasphere-ODS reverse phase C18 column and an ammonium acetate gradient system where buffer A was 10 mM ammonium acetate, pH 6.9 and buffer B was 20 mM ammonium acetate: acetonitrile 50:50; the gradient was 0–75% B over 75 min at a flow rate of 1.0 ml/min.

Endoproteinase-Lys C. The protein was dissolved in 0.1M ammonium bicarbonate buffer, pH 9.0 and endoproteinase-Lys C was added at a ratio of 1:100. Incubation proceeded at 37° C. for 1-2 hours after which another aliquot of endoproteinase-Lys C was added and incubation continued overnight. The mixture was then applied to a Hibar reverse phase C18 column and fractions were eluted using TFA gradient 25–100% B over 70 minutes.

Endoproteinase-Arg C. The digestion procedure with this protease was similar to that for endoproteinase-Lys C, except that the pH was 8.0-8.5 and the ratio used was 1:50.

Endoproteinase-Glu C. Digestion with this protease was performed in 50 mM sodium phosphate, pH 7.8 using a ratio of 1:100. The mixture was separated on a C18 column using a TFA gradient 20–100% B over 90 min. at a flow rate of 1.0 ml per min., where buffer A was 0.1% TFA and buffer B was 0.1% TFA in 80% acetonitrile.

Oligonucleotides. Oligonucleotides SEQ ID NO: 2 (5' GCRTTYTCRAARTCRTTYTC 3') and (SEQ ID NO: 3), where N is A, G, T, or C, R is A or G, and Y is C or T, were synthesized at Queen's University, based on the complementary sequences to SEQ ID NO: 8 (amino acids 161–167) and SEQ ID NO: 8 (amino acids 479–484) respectively. Oligonucleotides SEQ ID NO: 4, 5 EA ID NO: 5, SEQ ID NO: 6, (5' GGGGATCCTATCTAAAGCTACTTCA) were synthesized at the Syracuse University DNA and Protein amino acid sequence SEQ ID NO: 7 using the best codon frequencies from the sequence of the bases coding for the C-terminal 420 amino acids, while oligonucleotides SEQ ID NO: 5 and SEQ ID NO: 6 were based on DNA sequence. Southern Blots. Southern blots were done using the ECL kit except when the oligonucleotides were used as probes, when the method of Wallace and Miyada was used. Construction and Screening of *L. mesenteroides* libraries. *L. mesenteroides* genomic DNA was isolated by the method of Murphy et al., J. Baceriol. 169:334–339. Restriction fragments of 3.5–10.0kb were isolated (using Geneclean) from an Mbol partial digest and ligated to BamHI cut phosphatase treated pUC9. The ligation mixture was used to transform DH5α. Recombinant plasmids from transformed cells were separated from religated pUC9 by gel electrophoresis, isolated (using Geneclean), and transformed back into DH5α. The library was screened with oligonucleotides SEQ ID NO: 2 and SEQ ID NO: 3 by the method of Wallace and Miyada Methods Enzymol. 152:432–442.

Genomic libraries in μGEM11 were made by ligating electroeluted 14–20 Kb fragments of an Mbol partial digest to the BamHl λarms. The λ libraries were screened by the method of Wahl and Berger Methods Enzymol. 152:415–423.

DNA techniques Isolation of plasmids and plasmid transformations were performed as described. The procedures of Sambrook et al., *Molecular Cloning: A Laboratory Manual*, 2nd Ed. Cold Spring Harbor Laboratory Press, Cold Spring Harbor, N.Y. were used for standard DNA protocols. Polymerase Chain Reaction The polymerase chain reaction was done on an Ericomp Twinblock System for 30 cycles, each cycle consisting of 1' at 94° C., 1' at 42° C., and 5' at 68° C.

DNA Sequencing. DNA sequencing was done by the method of Sanger et al. *Proc. Natl. Acad. Sci. U.S.A.* 74:5463–5467 on M13 subclones or on double stranded DNA using either the Klenow fragment or Sequenase Assays of Glc6PD Activity Enzyme activity was measured at 25° by following the appearance of NADPH at 340 nm. Assays were initiated by the addition of enzyme to 1.0 ml of solution containing 33 mM Tris Cl (pH 7.6), 1.6 mM Glc6P, and 114 μM NADP$^+$.

RESULTS

Cloning of the glucose-6-phosphate dehydrogenase gene The amplified *L. mesenteroides* pUC9 library was screened using oligonucleotides SEQ ID NO: 2 and SEQ ID NO: 3. After an initial screen and a rescreen, five clones were isolated. Restriction analysis of the clones revealed that all contained an identical 5.3 kb insert (FIG. 1). A Southern blot of the clone (plmzΔN65) revealed that both oligonucleotides hybridized at one end of the insert (data not shown). Sequencing of the clone in this region revealed that it lacked the bases coding for the 65 N-terminal amino acids and the upstream DNA. The insert was sequenced over the coding region present and the downstream region (FIG. 1).

To obtain a full length, clone two λGEM 11 libraries were screened One library in *E. coli* strain MB406 was screened with the EcoRl-Sphl fragment of pLmzΔN65. Clones isolated from this library did not contain the DNA encoding the N-terminal amino acids. The other library, in *E. coli* strain LE392, was screened with the Eco Rl Sphl fragment and oligonucleotide SEQ ID NO: 4, No clones were isolated that hybridized to oligonucleotide SEQ ID NO: 4, although this probe did hybridize to *L. mesenteroides* genomic DNA on a Southern blot (data not shown). A possible explanation for the difficulty in cloning the entire Glc6PD gene is that the *L. mesenteroides* DNA may contain modified DNA sequences that are cleaved by *E. coli* restriction enzyme systems.

Southern analysis of *L. mesenteroides* DNA by the Eco Rl-Sphl fragment and oligonucleotide SEQ ID NO: 4 gave a partial map of restriction sites upstream from the gene (data not shown). An Nsi l site located 2.7 kb upstream from the start of the gene was found. Nsil-Sphl digests of *L. mesenteroides* genomic DNA produced 4.4 kb fragments containing the Glc6PD gene that were isolated by electroelution, ligated to pUC19, and transformed into E. coli strain DH5αMCR which lacks three known restriction enzymes that cleave modified DNA. No clones containing the Glc6PD gene were isolated.

To obtain unmodified DNA of the gene, 4.5 Kb NsiI SeaI fragments containing the entire Glc6PD gene were isolated by electroelution and ligated to pUC19. The recombinant plasmids were linearized and then amplified by PCR using oligonucleotide SEQ ID NO: 5 which is complementary to the downstream DNA sequence and the reverse sequencing primer. No PCR product was observed, presumably due to the length (4.4 kb) of the desired product. Oligonucleotide SEQ ID NO: 4, previously used to screen a λ library and for southern analysis of the upstream DNA, and the reverse primer were used to amplify the upstream DNA (FIG. 2A). A 2.7 Kb PCR product was isolated by electroelution and partially sequenced using oligonucleotide SEQ ID NO: 4 as the primer (FIG. 2A). Oligonucleotide SEQ ID NO: 6 based on the upstream DNA sequence of the PCR product and containing an engineered BamHl site, and oligonucleotide SEQ ID NO: 5 were used in a PCR on L. mesenteroides genomic DNA to amplify the entire gene (FIG. 2B). A 1.8 Kb PCR fragment was isolated, digested by BamHl and Sphl, ligated to pUC19, and transformed into DH5αMCR. Transformed colonies containing the recombinant plasmid (pLmz) had Glc6PD activity that could utilize either NAD+ or NADP+. The NAD+ reaction had 1.8 times the specific activity of the NADP+ reaction, this is characteristic of L. mesenteroides Glc6PD.

Sequencing of pLmz showed that the entire gene was present (FIG. 2B). The sequence of the gene shows the enzyme is composed of 485 amino acids (FIG. 3). The codon usage of the L. mesenteroides Glc6PD gene is given in Table 1. Putative transcription and translation initiation sites are seen and may explain the presence of enzyme activity. The specific activity of DH5αMCRL/pLmz (with NADP+ as coenzyme) is over 5000 times that of DH5αMCR (data not shown).

DISCUSSION

The L. mesenteroides Glc6PD gene encodes a polypeptide of 485 amino acids. The subunit molecular weight determined by the DNA sequence is 54,316 which corresponds well to the experimental value of 54,800. The isoelectric point of 4.7 also corresponds to the experimental value of 4.6. The enzyme differs from other Glc6PDs in that it can utilize either NAD+ or NADP+ as coenzyme. A comparison to the human erythrocyte Glc6PD shows that 33% of the amino acids are identical (FIG. 4) The hydrophobicities of the two enzymes are similar (FIG. 5). The human erythrocyte Glc6PD is NADP+ specific and is inhibited by steroids which do not inhibit the L. mesenteroides enzyme.

The partial clone (pLmzΔN65) was obtained using oligonucleotides based on amino acid sequences that contained errors. However, the oligonucleotides were still able to hybridize to only the Glc6PD gene.

The difficulty in cloning the entire gene may have resulted from the restriction, by E. coli host cells on L. mesenteroides DNA. The L. mesenteroides genomic DNA may be modified on a site that is recognized by an unidentified E. coli restriction system present in strain DH5αMCR. This would explain the difficulty in cloning the DNA upstream to the gene and the portion of the gene encoding the 65 N-terminal amino acids. By using PCR to amplify the gene with unmodified nucleotides, the E. coli could accept the L. mesenteroides Glc6PD gene. The expression of L. mesenteroides Glc6PD in E. coli is due to the presence of the appropriate transcription and translation sequences.

The previous paper reporting the cloning of the L. mesenteroides Glc6PD did not include a sequence of the cloned gene. The restriction map given in that paper is completely different from the one presented here. The authors present a 3.4 kb restriction map and localize the gene to a 2.4 kb fragment. Their restriction map contains sites not present in pLmz and the location and orientation of common sites is not the same. The authors do not indicate the relative specific activities of the NAD+ and NADP+ reactions (which were not measured by appearance of NADH or NADPH at 340 nm) and present no DNA or amino acid sequence information. The properties of the pLmz gene product are consistent with the physical properties of L. mesenteroides Glc6PD, the molecular weight, isoelectric point, amino acid sequence (including the absence of cysteine residues), and enzyme activity ratios with respect to NAD+ and NADP+ are the same indicating we have cloned the L. mesenteroides Glc6PD gene.

While this invention has been explained with reference to the structure disclosed herein, it is not confined to the details as set forth and this application is intended to cover any modifications and changes as may come within the scope of the following claims.

What is claimed is:

1. A method of producing Glucose-6-phosphate dehydrogenase from *L. mesenteroides*, comprising the steps of:

preparing oligonucleotides in accordance with peptide sequences of *L. mesenteroides* Glc6PD that are complementary to the upstream and downstream DNA sequence of an *L. mesenteroides* Glc6PD gene;

preparing a genomic library of *L. mesenteroides* DNA;

screening said genomic library with said oligonucleotides to isolate *L. mesenteroides* genomic DNA that contains the *L. mesenteroides* Glc6PD gene;

subjecting said isolated DNA to the polymerase chain reaction to produce an amplified DNA containing the Glc6PD gene;

digesting said amplified DNA with BamHI and SphI restriction endonucleases to produce a restriction fragment;

ligating said restriction fragment to a plasmid;

introducing said plasmid into a suitable strain of *E. coli*;

culturing said *E. coli*; and isolating *L. mesenteroides* Glc6PD from said cultures of *E. coli*.

2. The method of claim 1 wherein said oligonucleotides are SEQ ID NO: 5 and SEQ ID NO: 6.

3. An isolated and purified oligonucleotide consisting essentially of the sequence of SEQ ID NO: 4.

4. An isolated and purified oligonucleotide consisting essentially of the sequence of SEQ ID NO: 5.

5. An isolated and purified oligonucleotide consisting essentially of the sequence of SEQ ID NO: 6.

6. An isolated and purified DNA segment consisting essentially of the sequence of SEQ ID NO: 1.

7. An isolated and purified DNA segment consisting essentially of the sequence of SEQ ID NO: 10.

8. An isolated and purified DNA segment consisting essentially of the sequence of SEQ ID NO: 2.

9. An isolated and purified DNA segment consisting essentially of the sequence of SEQ ID NO: 3.

* * * * *

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 1970
        ( B ) TYPE: Nucleic acid
        ( C ) STRANDEDNESS: Double
        ( D ) TOPOLOGY: Linear ( i i ) MOLECULE TYPE: Genomic DNA ( i i i ) HYPOTHETICAL: No ( i v ) ANTI-SENSE: No (v) FRAGMENT TYPE: Not applicable (vi) ORIGINAL SOURCE:
  (A) ORGANISM: Leuconostoc mesenteroides
  (B) STRAIN: ATCC 12291

(vii) IMMEDIATE SOURCE:
  (A) LIBRARY: pLm2

(viii) POSITION IN GENOME: unknown (x) PUBLICATION INFORMATION: None (xi) SEQUENCE DESCRIPTION: SEQ ID NO: 1:

| | | | | | |
|---|---|---|---|---|---|
| GGATCCTATC | TAAAAGCTAC | TTCATTTGTT | GTACTCCTCA | TTTGCTTTTT | 50 |
| TATTATTGTG | TAACGAACAG | GTGATAAGGT | CAAGTGCAAA | ATTTCACGAC | 100 |
| AGATATCCAA | TTTTAGATGA | TAAACGTTTA | AAAAACGCTG | AAAACGGTTA | 150 |
| CTTTTTCCGC | TATTTTGCGC | TATAATGAAA | AGTGAATTTA | ACTAAAAATA | 200 |
| AGGGGTACAT | CATG       |            |            |            | 214 |

```
GTT TCA GAA ATC AAG ACG TTA GTA ACT TTC TTT GGT                           250
Val Ser Glu Ile Lys Thr Leu Val Thr Phe Phe Gly

GGC ACT GGT GAC TTG GCC AAG CGT AAG CTT TAC CCA TCA GTT TTC AAT           298
Gly Thr Gly Asp Leu Ala Lys Arg Lys Leu Tyr Pro Ser Val Phe Asn

CTT TAT AAA AAA GGC TAC TTG CAA AAG CAT TTT GCC ATT GTT GGA ACG           346
Leu Tyr Lys Lys Gly Tyr Leu Gln Lys His Phe Ala Ile Val Gly Thr

GCC CGT CAA GCC CTC AAT GAT GAC GAA TTC AAA CAA TTG GTT CGT GAT           394
Ala Arg Gln Ala Leu Asn Asp Asp Glu Phe Lys Gln Leu Val Arg Asp

TCA ATT AAA GAT TTC ACT GAC GAT CAA GCA CAA GCT GAG GCG TTC ATC           442
Ser Ile Lys Asp Phe Thr Asp Asp Gln Ala Gln Ala Glu Ala Phe Ile

GAA CAT TTC TCA TAC CGT GCA CAC GAC GTA ACA GAT GCT GCT TCA TAC           490
Glu His Phe Ser Tyr Arg Ala His Asp Val Thr Asp Ala Ala Ser Tyr

GCT GTT TTA AAA GAG GCG ATT GAA GAA GCT GCC GAC AAA TTT GAT ATC           538
Ala Val Leu Lys Glu Ala Ile Glu Glu Ala Ala Asp Lys Phe Asp Ile

GAT GGC AAC CGC ATT TTC TAT ATG TCA GTT GCG CCA CGT TTC TTT GGT           586
Asp Gly Asn Arg Ile Phe Tyr Met Ser Val Ala Pro Arg Phe Phe Gly

ACA ATT GCC AAA TAT CTT AAG TCA GAA GGC CTA CTA GCT GAC ACT GGT           634
Thr Ile Ala Lys Tyr Leu Lys Ser Glu Gly Leu Leu Ala Asp Thr Gly

TAC AAC CGT TTG ATG ATT GAA AAG CCT TTC GGT ACA TCA TAT GAC ACA           682
Tyr Asn Arg Leu Met Ile Glu Lys Pro Phe Gly Thr Ser Tyr Asp Thr

GCT GCC GAA CTC CAA AAT GAC TTG GAA AAC GCA TTT GAT GAT AAC CAA           730
Ala Ala Glu Leu Gln Asn Asp Leu Glu Asn Ala Phe Asp Asp Asn Gln

CTA TTC CGT ATT GAC CAC TAC CTT GGT AAG GAA ATG GTT CAA AAC ATT           778
Leu Phe Arg Ile Asp His Tyr Leu Gly Lys Glu Met Val Gln Asn Ile

GCT GCC CTT CGC TTT GGT AAC CCA ATT TTC GAT GCT GCT TGG AAC AAG           826
Ala Ala Leu Arg Phe Gly Asn Pro Ile Phe Asp Ala Ala Trp Asn Lys

GAT TAC ATC AAG AAC GTT CAA GTA ACA TTG TCA GAA GTC TTG GGT GTC           874
Asp Tyr Ile Lys Asn Val Gln Val Thr Leu Ser Glu Val Leu Gly Val

GAA GAA CGT GCC GGC TAC TAT GAC ACA GCC GGT GCA TTG CTT GAC ATG           922
Glu Glu Arg Ala Gly Tyr Tyr Asp Thr Ala Gly Ala Leu Leu Asp Met

ATT CAA AAC CAC ACC ATG CAA ATT GTT GGT TGG TTA GCC ATG GAA AAA           970
Ile Gln Asn His Thr Met Gln Ile Val Gly Trp Leu Ala Met Glu Lys

CCA GAA TCA TTC ACT GAC AAA GAC ATT CGT GCC GCT AAA AAC GCA GCC           1018
Pro Glu Ser Phe Thr Asp Lys Asp Ile Arg Ala Ala Lys Asn Ala Ala

TTT AAT GCT TTG AAG ATC TAT GAT GAA GCA GAA GTT AAC AAA TAC TTT           1066
Phe Asn Ala Leu Lys Ile Tyr Asp Glu Ala Glu Val Asn Lys Tyr Phe

GTT CGT GCA CAA TAT GGT GCC GGT GAT TCA GCT GAC TTC AAG CCA TAC           1114
Val Arg Ala Gln Tyr Gly Ala Gly Asp Ser Ala Asp Phe Lys Pro Tyr
```

-continued

```
CTT GAA GAA TTA GAC GTA CCT GCT GAT TCT AAA AAC AAT ACC TTC ATC      1162
Leu Glu Glu Leu Asp Val Pro Ala Asp Ser Lys Asn Asn Thr Phe Ile

GCC GGC GAA TTG CAA TTT GAT TTG CCA CGT TGG GAG GGT GTC CCA TTC      1210
Ala Gly Glu Leu Gln Phe Asp Leu Pro Arg Trp Glu Gly Val Pro Phe

TAT GTC CGT TCA GGT AAG CGC TTA GCT GCT AAA CAG ACA CGG GTT GAT      1258
Tyr Val Arg Ser Gly Lys Arg Leu Ala Ala Lys Gln Thr Arg Val Asp

ATC GTC TTT AAG GCT GGC ACG TTT AAC TTT GGT TCA GAA CAA GAA GCA      1306
Ile Val Phe Lys Ala Gly Thr Phe Asn Phe Gly Ser Glu Gln Glu Ala

CAA GAA GCT GTC TTG TCA ATT ATC ATT GAT CCA AAG GGT GCT ATC GAA      1354
Gln Glu Ala Val Leu Ser Ile Ile Ile Asp Pro Lys Gly Ala Ile Glu

TTG AAG TTG AAC GCC AAG TCA GTT GAA GAT GCT TTC AAC ACA CGT ACA      1402
Leu Lys Leu Asn Ala Lys Ser Val Glu Asp Ala Phe Asn Thr Arg Thr

ATT GAC TTA GGT TGG ACT GTA TCT GAC GAA GAT AAG AAG AAC ACG CCA      1450
Ile Asp Leu Gly Trp Thr Val Ser Asp Glu Asp Lys Lys Asn Thr Pro

GAA CCA TAC GAA CGT ATG ATT CAC GAC ACT ATG AAT GGT GAT GGC TCT      1498
Glu Pro Tyr Glu Arg Met Ile His Asp Thr Met Asn Gly Asp Gly Ser

AAC TTC GCT GAC TGG AAT GGC GTT TCA ATC GCT TGG AAG TTC GTT GAT      1546
Asn Phe Ala Asp Trp Asn Gly Val Ser Ile Ala Trp Lys Phe Val Asp

GCT ATT TCA GCC GTT TAT ACC GCA GAT AAA GCA CCA CTT GAA ACT TAC      1594
Ala Ile Ser Ala Val Tyr Thr Ala Asp Lys Ala Pro Leu Glu Thr Tyr

AAG TCG GGC TCA ATG GGT CCT GAA GCA TCC GAT AAA TTA TTG GCT GCC      1642
Lys Ser Gly Ser Met Gly Pro Glu Ala Ser Asp Lys Leu Leu Ala Ala

AAT GGT GAT GCT TGG GTG TTT AAA GGT                                  1669
Asn Gly Asp Ala Trp Val Phe Lys Gly

TAATTAAAGC CCCAAAAAAA CGATCGATTG TGATCGTTTT TTTATTGCCC                1719

AATTTACACA GTTTCATCAA GAATCCGTTT TGTTTCACGA AAAACAGCCG                1769

CTAAGTTTTT GTACTGATCC GCATGCAGCA CAACAGTAAC AAAGTGATGC                1819

TTTTTGTACG TAAAGAACCC AACAAATGAC ACACCAGATT TAACAGAAAC                1869

ACCTAATTTA CCACCCGTGA CCTGATATTT TGTCTGACTA AAATAGTTAT                1919

TCATTAGTGA AAAAATTTGA CGCTTGAGTT GTGCCATTGA AAGTGGGGAT                1969

C                                                                    1970
```

( 2 ) INFORMATION FOR SEQ ID NO: 2:

( i ) SEQUENCE CHARACTERISTICS:
        ( A ) LENGTH: 20
        ( B ) TYPE: Nucleic Acid
        ( C ) STRANDEDNESS: Double
        ( D ) TOPOLOGY: Linear ( i i ) MOLECULE TYPE: Synthetic Oligonucleotide ( i i i ) HYPOTHETICAL: No ( i v ) ANTI-SENSE: No ( v ) FRAGMENT TYPE: Not applicable ( v i ) ORIGINAL SOURCE: Not applicable ( v i i ) IMMEDIATE SOURCE: Not applicable ( v i i i ) POSITION IN GENOME: Not applicable ( x ) PUBLICATION INFORMATION: None ( x i ) SEQUENCE DESCRIPTION: SEQ ID NO: 2:

```
GCRTTYTCRA ARTCRTTYTC          20
```

( 2 ) INFORMATION FOR SEQ ID NO: 3:

( i ) SEQUENCE CHARACTERISTICS:
    ( A ) LENGTH: 18
    ( B ) TYPE: Nucleic Acid
    ( C ) STRANDEDNESS: Double
    ( D ) TOPOLOGY: Linear:4

( i i ) MOLECULE TYPE: Synthetic Oligonucleotide ( i i i ) HYPOTHETICAL: No ( i v ) ANTI-SENSE: No ( v ) FRAGMENT TYPE: Not applicable ( v i ) ORIGINAL SOURCE: Not applicable ( v i i ) IMMEDIATE SOURCE: Not applicable ( v i i i ) POSITION IN GENOME: Not applicable ( x ) PUBLICATION INFORMATION: None ( x i ) SEQUENCE DESCRIPTION: SEQ ID NO: 3:

CCARAANACC CANGCRTC            18

( 2 ) INFORMATION FOR SEQ ID NO: 4:

( i ) SEQUENCE CHARACTERISTICS:
        ( A ) LENGTH: 47
        ( B ) TYPE: Nucleic Acid
        ( C ) STRANDEDNESS: double
        ( D ) TOPOLOGY: Linear ( i i ) MOLECULE TYPE: Synthetic Oligonucleotide ( i i i ) HYPOTHETICAL: No ( i v ) ANTI-SENSE: No ( v ) FRAGMENT TYPE: Not applicable ( v i ) ORIGINAL SOURCE:

( v i i ) IMMEDIATE SOURCE: Not applicable ( v i i i ) POSITION IN GENOME: Not applicable ( x ) PUBLICATION INFORMATION: None ( x i ) SEQUENCE DESCRIPTION: SEQ ID NO: 4:

TCACCTGTAC CACCGAAGAA TGTAACCAAT GTCTTAATTT CTGAAAC            47

( 2 ) INFORMATION FOR SEQ ID NO: 5:

( i ) SEQUENCE CHARACTERISTICS:
        ( A ) LENGTH: 23
        ( B ) TYPE: Nucleic Acid
        ( C ) STRANDEDNESS: Double
        ( D ) TOPOLOGY: Linear ( i i ) MOLECULE TYPE: Synthetic Oligonucleotide ( i i i ) HYPOTHETICAL: No ( i v ) ANTI-SENSE: No ( v ) FRAGMENT TYPE: Not applicable ( v i ) ORIGINAL SOURCE:

( v i i ) IMMEDIATE SOURCE: Not applicable ( v i i i ) POSITION IN GENOME: Not applicable ( x ) PUBLICATION INFORMATION: None ( x i ) SEQUENCE DESCRIPTION: SEQ ID NO: 5:

CTGGTGTGTC ATTTGTTGGG TTC    23

(2) INFORMATION FOR SEQ ID NO: 6:

(i) SEQUENCE CHARACTERISTICS:
        (A) LENGTH: 26
        (B) TYPE: Nucleic Acid
        (C) STRANDEDNESS: Double
        (D) TOPOLOGY: Linear (ii) MOLECULE TYPE: Synthetic Oligonucleotide (iii) HYPOTHETICAL: No (iv) ANTI-SENSE: No (v) FRAGMENT TYPE: Not applicable (vi) ORIGINAL SOURCE: Not applicable (vii) IMMEDIATE SOURCE: Not applicable (viii) POSITION IN GENOME: Not applicable (x) PUBLICATION INFORMATION: None (xi) SEQUENCE DESCRIPTION: SEQ ID NO: 6:

GGGGATCCTA TCTAAAAGCT ACTTCA    26

(2) INFORMATION FOR SEQ ID NO: 7:

(i) SEQUENCE CHARACTERISTICS:
        (A) LENGTH: 16
        (B) TYPE: Amino Acid
        (C) STRANDEDNESS: Not applicable
        (D) TOPOLOGY: Linear (ii) MOLECULE TYPE: peptide (iii) HYPOTHETICAL: no (iv) ANTI-SENSE: Not applicable (v) FRAGMENT TYPE: N-terminal (vi) ORIGINAL SOURCE: Leuconostoc mesenteroides glucose 6- phosphate dehydrogenase (vii) IMMEDIATE SOURCE: Not applicable (viii) POSITION IN GENOME: Not applicable (x) PUBLICATION INFORMATION: None (xi) SEQUENCE DESCRIPTION: SEQ ID NO: 7:

Val Ser Glu Ile Lys Thr Leu Val Thr Phe Phe Gly Gly Thr Gly Asp
1           5                      10                  15

(2) INFORMATION FOR SEQ ID NO: 8:

(i) SEQUENCE CHARACTERISTICS:
        (A) LENGTH: 7
        (B) TYPE: Amino Acid
        (C) STRANDEDNESS: Not applicable
        (D) TOPOLOGY: Linear (ii) MOLECULE TYPE: amino acid (iii) HYPOTHETICAL: no (iv) ANTI-SENSE: Not applicable (v) FRAGMENT TYPE: internal (vi) ORIGINAL SOURCE: Leuconostoc mesenteroides glucose 6- phosphate dehydrogenase (v i i) IMMEDIATE SOURCE: Not applicable (v i i i) POSITION IN GENOME: Not applicable (x) PUBLICATION INFORMATION: None (x i) SEQUENCE DESCRIPTION: SEQ ID NO: 8:

Glu Asn Asp Phe Glu Asn Ala
1                   5

(2) INFORMATION FOR SEQ ID NO: 9:

(i) SEQUENCE CHARACTERISTICS:
        (A) LENGTH: 6
        (B) TYPE: Amino Acid
        (C) STRANDEDNESS: Not applicable
        (D) TOPOLOGY: Linear (i i) MOLECULE TYPE: amino acid (i i i) HYPOTHETICAL: no (i v) ANTI-SENSE: Not applicable (v) FRAGMENT TYPE: internal (v i) ORIGINAL SOURCE: Leuconostoc mesenteroides glucose 6- phosphate
                              dehydrogenase (v i i) IMMEDIATE SOURCE: Not applicable (v i i i) POSITION IN GENOME: Not applicable (x) PUBLICATION INFORMATION: None (x i) SEQUENCE DESCRIPTION: SEQ ID NO: 9:

Asp Ala Trp Val Phe Trp
1                   5

(2) INFORMATION FOR SEQ ID NO: 10:

(i) SEQUENCE CHARACTERISTICS:
        (A) LENGTH: 1461
        (B) TYPE: Nucleic Acid
        (C) STRANDEDNESS: Double
        (D) TOPOLOGY: Linear (i i) MOLECULE TYPE: Genomic DNA (i i i) HYPOTHETICAL: No (i v) ANTI-SENSE: No (v) FRAGMENT TYPE: Not applicable (v i) ORIGINAL SOURCE:
        (A) ORGANISM: Leuconostoc mesenteroides
        (B) STRAIN: ATCC 12291

(v i i) IMMEDIATE SOURCE:
        (A) LIBRARY: pLm2

(v i i i) POSITION IN GENOME: unknown (x) PUBLICATION INFORMATION: None (x i) SEQUENCE DESCRIPTION: SEQ ID NO: 10:

```
ATG                                                                               3

GTT  TCA  GAA  ATC  AAG  ACG  TTA  GTA  ACT  TTC  TTT  GGT                       39
Val  Ser  Glu  Ile  Lys  Thr  Leu  Val  Thr  Phe  Phe  Gly

GGC  ACT  GGT  GAC  TTG  GCC  AAG  CGT  AAG  CTT  TAC  CCA  TCA  GTT  TTC  AAT   87
Gly  Thr  Gly  Asp  Leu  Ala  Lys  Arg  Lys  Leu  Tyr  Pro  Ser  Val  Phe  Asn

CTT  TAT  AAA  AAA  GGC  TAC  TTG  CAA  AAG  CAT  TTT  GCC  ATT  GTT  GGA  ACG  135
```

| | | | | | | | | | | | | | | | | |
|---|---|---|---|---|---|---|---|---|---|---|---|---|---|---|---|---|
| Leu | Tyr | Lys | Lys | Gly | Tyr | Leu | Gln | Lys | His | Phe | Ala | Ile | Val | Gly | Thr | |
| GCC | CGT | CAA | GCC | CTC | AAT | GAT | GAC | GAA | TTC | AAA | CAA | TTG | GTT | CGT | GAT | 183 |
| Ala | Arg | Gln | Ala | Leu | Asn | Asp | Asp | Glu | Phe | Lys | Gln | Leu | Val | Arg | Asp | |
| TCA | ATT | AAA | GAT | TTC | ACT | GAC | GAT | CAA | GCA | CAA | GCT | GAG | GCG | TTC | ATC | 231 |
| Ser | Ile | Lys | Asp | Phe | Thr | Asp | Asp | Gln | Ala | Gln | Ala | Glu | Ala | Phe | Ile | |
| GAA | CAT | TTC | TCA | TAC | CGT | GCA | CAC | GAC | GTA | ACA | GAT | GCT | GCT | TCA | TAC | 279 |
| Glu | His | Phe | Ser | Tyr | Arg | Ala | His | Asp | Val | Thr | Asp | Ala | Ala | Ser | Tyr | |
| GCT | GTT | TTA | AAA | GAG | GCG | ATT | GAA | GAA | GCT | GCC | GAC | AAA | TTT | GAT | ATC | 327 |
| Ala | Val | Leu | Lys | Glu | Ala | Ile | Glu | Glu | Ala | Ala | Asp | Lys | Phe | Asp | Ile | |
| GAT | GGC | AAC | CGC | ATT | TTC | TAT | ATG | TCA | GTT | GCG | CCA | CGT | TTC | TTT | GGT | 375 |
| Asp | Gly | Asn | Arg | Ile | Phe | Tyr | Met | Ser | Val | Ala | Pro | Arg | Phe | Phe | Gly | |
| ACA | ATT | GCC | AAA | TAT | CTT | AAG | TCA | GAA | GGC | CTA | CTA | GCT | GAC | ACT | GGT | 423 |
| Thr | Ile | Ala | Lys | Tyr | Leu | Lys | Ser | Glu | Gly | Leu | Leu | Ala | Asp | Thr | Gly | |
| TAC | AAC | CGT | TTG | ATG | ATT | GAA | AAG | CCT | TTC | GGT | ACA | TCA | TAT | GAC | ACA | 471 |
| Tyr | Asn | Arg | Leu | Met | Ile | Glu | Lys | Pro | Phe | Gly | Thr | Ser | Tyr | Asp | Thr | |
| GCT | GCC | GAA | CTC | CAA | AAT | GAC | TTG | GAA | AAC | GCA | TTT | GAT | GAT | AAC | CAA | 519 |
| Ala | Ala | Glu | Leu | Gln | Asn | Asp | Leu | Glu | Asn | Ala | Phe | Asp | Asp | Asn | Gln | |
| CTA | TTC | CGT | ATT | GAC | CAC | TAC | CTT | GGT | AAG | GAA | ATG | GTT | CAA | AAC | ATT | 567 |
| Leu | Phe | Arg | Ile | Asp | His | Tyr | Leu | Gly | Lys | Glu | Met | Val | Gln | Asn | Ile | |
| GCT | GCC | CTT | CGC | TTT | GGT | AAC | CCA | ATT | TTC | GAT | GCT | GCT | TGG | AAC | AAG | 615 |
| Ala | Ala | Leu | Arg | Phe | Gly | Asn | Pro | Ile | Phe | Asp | Ala | Ala | Trp | Asn | Lys | |
| GAT | TAC | ATC | AAG | AAC | GTT | CAA | GTA | ACA | TTG | TCA | GAA | GTC | TTG | GGT | GTC | 663 |
| Asp | Tyr | Ile | Lys | Asn | Val | Gln | Val | Thr | Leu | Ser | Glu | Val | Leu | Gly | Val | |
| GAA | GAA | CGT | GCC | GGC | TAC | TAT | GAC | ACA | GCC | GGT | GCA | TTG | CTT | GAC | ATG | 711 |
| Glu | Glu | Arg | Ala | Gly | Tyr | Tyr | Asp | Thr | Ala | Gly | Ala | Leu | Leu | Asp | Met | |
| ATT | CAA | AAC | CAC | ACC | ATG | CAA | ATT | GTT | GGT | TGG | TTA | GCC | ATG | GAA | AAA | 759 |
| Ile | Gln | Asn | His | Thr | Met | Gln | Ile | Val | Gly | Trp | Leu | Ala | Met | Glu | Lys | |
| CCA | GAA | TCA | TTC | ACT | GAC | AAA | GAC | ATT | CGT | GCC | GCT | AAA | AAC | GCA | GCC | 807 |
| Pro | Glu | Ser | Phe | Thr | Asp | Lys | Asp | Ile | Arg | Ala | Ala | Lys | Asn | Ala | Ala | |
| TTT | AAT | GCT | TTG | AAG | ATC | TAT | GAT | GAA | GCA | GAA | GTT | AAC | AAA | TAC | TTT | 855 |
| Phe | Asn | Ala | Leu | Lys | Ile | Tyr | Asp | Glu | Ala | Glu | Val | Asn | Lys | Tyr | Phe | |
| GTT | CGT | GCA | CAA | TAT | GGT | GCC | GGT | GAT | TCA | GCT | GAC | TTC | AAG | CCA | TAC | 903 |
| Val | Arg | Ala | Gln | Tyr | Gly | Ala | Gly | Asp | Ser | Ala | Asp | Phe | Lys | Pro | Tyr | |
| CTT | GAA | GAA | TTA | GAC | GTA | CCT | GCT | GAT | TCT | AAA | AAC | AAT | ACC | TTC | ATC | 951 |
| Leu | Glu | Glu | Leu | Asp | Val | Pro | Ala | Asp | Ser | Lys | Asn | Asn | Thr | Phe | Ile | |
| GCC | GGC | GAA | TTG | CAA | TTT | GAT | TTG | CCA | CGT | TGG | GAG | GGT | GTC | CCA | TTC | 999 |
| Ala | Gly | Glu | Leu | Gln | Phe | Asp | Leu | Pro | Arg | Trp | Glu | Gly | Val | Pro | Phe | |
| TAT | GTC | CGT | TCA | GGT | AAG | CGC | TTA | GCT | GCT | AAA | CAG | ACA | CGG | GTT | GAT | 1047 |
| Tyr | Val | Arg | Ser | Gly | Lys | Arg | Leu | Ala | Ala | Lys | Gln | Thr | Arg | Val | Asp | |
| ATC | GTC | TTT | AAG | GCT | GGC | ACG | TTT | AAC | TTT | GGT | TCA | GAA | CAA | GAA | GCA | 1095 |
| Ile | Val | Phe | Lys | Ala | Gly | Thr | Phe | Asn | Phe | Gly | Ser | Glu | Gln | Glu | Ala | |
| CAA | GAA | GCT | GTC | TTG | TCA | ATT | ATC | ATT | GAT | CCA | AAG | GGT | GCT | ATC | GAA | 1143 |
| Gln | Glu | Ala | Val | Leu | Ser | Ile | Ile | Ile | Asp | Pro | Lys | Gly | Ala | Ile | Glu | |
| TTG | AAG | TTG | AAC | GCC | AAG | TCA | GTT | GAA | GAT | GCT | TTC | AAC | ACA | CGT | ACA | 1191 |
| Leu | Lys | Leu | Asn | Ala | Lys | Ser | Val | Glu | Asp | Ala | Phe | Asn | Thr | Arg | Thr | |
| ATT | GAC | TTA | GGT | TGG | ACT | GTA | TCT | GAC | GAA | GAT | AAG | AAG | AAC | ACG | CCA | 1239 |
| Ile | Asp | Leu | Gly | Trp | Thr | Val | Ser | Asp | Glu | Asp | Lys | Lys | Asn | Thr | Pro | |
| GAA | CCA | TAC | GAA | CGT | ATG | ATT | CAC | GAC | ACT | ATG | AAT | GGT | GAT | GGC | TCT | 1287 |
| Glu | Pro | Tyr | Glu | Arg | Met | Ile | His | Asp | Thr | Met | Asn | Gly | Asp | Gly | Ser | |
| AAC | TTC | GCT | GAC | TGG | AAT | GGC | GTT | TCA | ATC | GCT | TGG | AAG | TTC | GTT | GAT | 1335 |
| Asn | Phe | Ala | Asp | Trp | Asn | Gly | Val | Ser | Ile | Ala | Trp | Lys | Phe | Val | Asp | |
| GCT | ATT | TCA | GCC | GTT | TAT | ACC | GCA | GAT | AAA | GCA | CCA | CTT | GAA | ACT | TAC | 1383 |
| Ala | Ile | Ser | Ala | Val | Tyr | Thr | Ala | Asp | Lys | Ala | Pro | Leu | Glu | Thr | Tyr | |
| AAG | TCG | GGC | TCA | ATG | GGT | CCT | GAA | GCA | TCC | GAT | AAA | TTA | TTG | GCT | GCC | 1431 |
| Lys | Ser | Gly | Ser | Met | Gly | Pro | Glu | Ala | Ser | Asp | Lys | Leu | Leu | Ala | Ala | |

```
AAT GGT GAT GCT TGG GTG TTT AAA GGT                              1458
Asn Gly Asp Ala Trp Val Phe Lys Gly

TAA                                                              1461
```